United States Patent
Esteller et al.

(10) Patent No.: US 11,623,095 B2
(45) Date of Patent: Apr. 11, 2023

(54) METHODS AND SYSTEMS FOR INTERLEAVING WAVEFORMS FOR ELECTRICAL STIMULATION AND MEASUREMENT

(71) Applicant: Boston Scientific Neuromodulation Corporation, Valencia, CA (US)

(72) Inventors: Rosana Esteller, Santa Clarita, CA (US); Goran N. Marnfeldt, Valencia, CA (US); Michael A. Moffitt, Solon, OH (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 129 days.

(21) Appl. No.: 16/907,052

(22) Filed: Jun. 19, 2020

(65) Prior Publication Data

US 2020/0398057 A1    Dec. 24, 2020

Related U.S. Application Data

(60) Provisional application No. 62/864,195, filed on Jun. 20, 2019.

(51) Int. Cl.
*A61N 1/36* (2006.01)
*A61N 1/05* (2006.01)

(52) U.S. Cl.
CPC ..... *A61N 1/36135* (2013.01); *A61N 1/36175* (2013.01); *A61N 1/36185* (2013.01); *A61N 1/36192* (2013.01); *A61N 1/0551* (2013.01)

(58) Field of Classification Search
CPC ................ A61N 1/0551; A61N 1/3605; A61N 1/36135; A61N 1/36139; A61N 1/36164;
(Continued)

(56) References Cited

U.S. PATENT DOCUMENTS

| 4,625,730 A | 12/1986 | Fountain et al. |
| 5,697,958 A | 12/1997 | Paul et al. |

(Continued)

FOREIGN PATENT DOCUMENTS

| EP | 3216489 A1 * | 9/2017 | ........... A61N 1/0551 |
| WO | 2006/119131 | 11/2006 | |

(Continued)

OTHER PUBLICATIONS

Invitation to Pay Additional Fees and Partial Search Report for PCT Application No. PCT/US2020/038811 dated Sep. 7, 2020.

(Continued)

*Primary Examiner* — Carl H Layno
*Assistant Examiner* — Jane C Kalinock
(74) *Attorney, Agent, or Firm* — Branch Partners PLLC; Bruce E. Black

(57) ABSTRACT

A system can utilize interleaving periods or waveforms to stimulate patient tissue and sense signals using the stimulation electrodes. For example, the system can utilize alternating therapeutic periods and sensing periods. As another example, the system can alternate between biphasic waveforms having opposite temporal orders of positive and negative phases. As another example, waveforms that differ in a parameter, such as amplitude or pulse width, can be interleaved to provide different information in the respective sensed signals.

20 Claims, 11 Drawing Sheets

(58) Field of Classification Search
CPC ............ A61N 1/36175; A61N 1/36185; A61N 1/36192; A61B 5/053; A61B 5/24; A61B 5/4836
USPC .......................................................... 607/59
See application file for complete search history.

(56) References Cited

U.S. PATENT DOCUMENTS

| | | | |
|---|---|---|---|
| 5,702,429 | A | 12/1997 | King |
| 5,902,236 | A | 5/1999 | Iverson |
| 5,902,249 | A | 5/1999 | Lyster |
| 5,913,882 | A | 6/1999 | King |
| 6,061,593 | A | 5/2000 | Fischell et al. |
| 6,181,969 | B1 | 1/2001 | Gord |
| 6,516,227 | B1 | 2/2003 | Meadows et al. |
| 6,560,490 | B2 | 5/2003 | Grill et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 6,895,280 | B2 | 5/2005 | Meadows et al. |
| 7,024,247 | B2 | 4/2006 | Gliner et al. |
| 7,136,695 | B2 | 11/2006 | Pless et al. |
| 7,244,150 | B1 | 7/2007 | Brase et al. |
| 7,424,322 | B2 | 9/2008 | Lombardi et al. |
| 7,437,193 | B2 | 10/2008 | Parramon et al. |
| 7,450,992 | B1 | 11/2008 | Cameron |
| 7,450,997 | B1 | 11/2008 | Pianca et al. |
| 7,603,179 | B1 | 10/2009 | Grandhe |
| 7,672,734 | B2 | 3/2010 | Anderson et al. |
| 7,761,165 | B1 | 7/2010 | He et al. |
| 7,783,359 | B2 | 8/2010 | Meadows |
| 7,792,590 | B1 | 9/2010 | Pianca et al. |
| 7,809,446 | B2 | 10/2010 | Meadows |
| 7,949,395 | B2 | 5/2011 | Kuzma |
| 7,974,706 | B2 | 7/2011 | Moffitt et al. |
| 8,175,710 | B2 | 5/2012 | He |
| 8,224,450 | B2 | 7/2012 | Brase |
| 8,255,057 | B2 | 8/2012 | Fang et al. |
| 8,271,094 | B1 | 9/2012 | Moffitt et al. |
| 8,295,944 | B2 | 10/2012 | Howard et al. |
| 8,335,664 | B2 | 12/2012 | Eberle |
| 8,352,030 | B2 | 1/2013 | Denison |
| 8,364,278 | B2 | 1/2013 | Pianca et al. |
| 8,391,985 | B2 | 3/2013 | McDonald |
| 8,606,362 | B2 | 12/2013 | He et al. |
| 8,620,436 | B2 | 12/2013 | Parramon et al. |
| 8,688,235 | B1 | 4/2014 | Pianca et al. |
| 8,768,453 | B2 | 7/2014 | Parramon et al. |
| 9,044,155 | B2 | 6/2015 | Strahl |
| 9,061,140 | B2 | 6/2015 | Shi et al. |
| 9,113,801 | B2 | 8/2015 | DiLorenzo |
| 9,119,964 | B2 | 9/2015 | Marnfeldt |
| 9,155,892 | B2 | 10/2015 | Parker et al. |
| 9,248,274 | B2 | 2/2016 | Troosters et al. |
| 9,248,279 | B2 | 2/2016 | Chen et al. |
| 9,265,431 | B2 | 2/2016 | Hincapie Ordonez et al. |
| 9,302,112 | B2 | 4/2016 | Bornzin et al. |
| 9,381,356 | B2 | 7/2016 | Parker et al. |
| 9,386,934 | B2 | 7/2016 | Parker et al. |
| 9,399,132 | B2 | 7/2016 | Parramon et al. |
| 9,403,013 | B2 | 8/2016 | Walker et al. |
| 9,409,020 | B2 | 8/2016 | Parker |
| 9,526,897 | B2 | 12/2016 | Chen et al. |
| 9,533,148 | B2 | 1/2017 | Carcieri |
| 9,731,116 | B2 | 8/2017 | Chen |
| 9,872,990 | B2 | 1/2018 | Parker et al. |
| 9,974,455 | B2 | 5/2018 | Parker et al. |
| 10,076,667 | B2 | 9/2018 | Kaula et al. |
| 2002/0156513 | A1 | 10/2002 | Borkan |
| 2003/0139781 | A1 | 7/2003 | Bradlet et al. |
| 2005/0113705 | A1 | 5/2005 | Fischell et al. |
| 2005/0246004 | A1 | 11/2005 | Cameron et al. |
| 2007/0150036 | A1 | 6/2007 | Anderson |
| 2008/0146894 | A1 | 6/2008 | Bulkes et al. |
| 2009/0187222 | A1 | 7/2009 | Barker |
| 2009/0216141 | A1 | 8/2009 | Fischell et al. |
| 2009/0276021 | A1 | 11/2009 | Meadows et al. |
| 2010/0076535 | A1 | 3/2010 | Pianca et al. |
| 2010/0114224 | A1* | 5/2010 | Krause ................ A61N 1/3605 607/8 |
| 2010/0268298 | A1 | 10/2010 | Moffitt et al. |
| 2010/0305642 | A1 | 12/2010 | Dong et al. |
| 2010/0331916 | A1* | 12/2010 | Parramon ............ A61N 1/3614 607/60 |
| 2011/0004267 | A1 | 1/2011 | Meadows |
| 2011/0005069 | A1 | 1/2011 | Pianca |
| 2011/0078900 | A1 | 4/2011 | Pianca et al. |
| 2011/0130817 | A1 | 6/2011 | Chen |
| 2011/0130818 | A1 | 6/2011 | Chen |
| 2011/0238129 | A1 | 9/2011 | Moffitt et al. |
| 2011/0313500 | A1 | 12/2011 | Barker et al. |
| 2012/0016378 | A1 | 1/2012 | Pianca et al. |
| 2012/0046710 | A1 | 2/2012 | DiGiore et al. |
| 2012/0071949 | A1 | 3/2012 | Pianca et al. |
| 2012/0092031 | A1 | 4/2012 | Shi et al. |
| 2012/0095519 | A1 | 4/2012 | Parramon et al. |
| 2012/0095529 | A1 | 4/2012 | Parramon et al. |
| 2012/0165911 | A1 | 6/2012 | Pianca |
| 2012/0197375 | A1 | 8/2012 | Pianca et al. |
| 2012/0203316 | A1 | 8/2012 | Moffitt et al. |
| 2012/0203320 | A1 | 8/2012 | DiGiore et al. |
| 2012/0203321 | A1 | 8/2012 | Moffitt et al. |
| 2012/0316615 | A1 | 12/2012 | DiGiore et al. |
| 2013/0105071 | A1 | 5/2013 | DiGiore et al. |
| 2013/0197602 | A1 | 8/2013 | Pianca et al. |
| 2013/0289665 | A1 | 10/2013 | Marnfeldt et al. |
| 2014/0031901 | A1 | 1/2014 | Zhu et al. |
| 2014/0194772 | A1 | 7/2014 | Single et al. |
| 2014/0236042 | A1 | 8/2014 | Parker et al. |
| 2014/0243926 | A1 | 8/2014 | Carcieri |
| 2014/0276707 | A1 | 9/2014 | Jaax |
| 2014/0277282 | A1 | 9/2014 | Jaax |
| 2014/0296737 | A1 | 10/2014 | Parker et al. |
| 2015/0018699 | A1 | 1/2015 | Zeng et al. |
| 2015/0119751 | A1 | 4/2015 | Stanslaski et al. |
| 2015/0157861 | A1 | 6/2015 | Aghassian |
| 2015/0282725 | A1 | 10/2015 | Single |
| 2015/0313487 | A1 | 11/2015 | Single et al. |
| 2015/0360038 | A1 | 12/2015 | Zottola et al. |
| 2016/0166164 | A1 | 6/2016 | Obradovic et al. |
| 2016/0287126 | A1 | 10/2016 | Parker et al. |
| 2016/0287182 | A1 | 10/2016 | Single |
| 2017/0049345 | A1 | 2/2017 | Single |
| 2017/0071490 | A1 | 3/2017 | Parker et al. |
| 2017/0113046 | A1 | 4/2017 | Fried et al. |
| 2017/0135624 | A1 | 5/2017 | Parker |
| 2017/0136243 | A1 | 5/2017 | Lee et al. |
| 2017/0157410 | A1 | 6/2017 | Moffitt et al. |
| 2017/0173335 | A1 | 6/2017 | Min et al. |
| 2017/0216587 | A1 | 8/2017 | Parker |
| 2017/0259065 | A1 | 9/2017 | Baru et al. |
| 2017/0281958 | A1 | 10/2017 | Serrano Carmona et al. |
| 2017/0296823 | A1 | 10/2017 | Hershey et al. |
| 2017/0361101 | A1 | 12/2017 | Single |
| 2018/0028083 | A1 | 2/2018 | Greenhut et al. |
| 2018/0071513 | A1 | 3/2018 | Weiss et al. |
| 2018/0071520 | A1 | 3/2018 | Weerakoon et al. |
| 2018/0071527 | A1 | 3/2018 | Feldman et al. |
| 2018/0071530 | A1 | 3/2018 | Giftakis et al. |
| 2018/0078769 | A1 | 3/2018 | Dinsmoor et al. |
| 2018/0110987 | A1 | 4/2018 | Parker |
| 2018/0117335 | A1 | 5/2018 | Parker et al. |
| 2018/0132747 | A1 | 5/2018 | Parker et al. |
| 2018/0132760 | A1 | 5/2018 | Parker |
| 2018/0133459 | A1 | 5/2018 | Parker et al. |
| 2018/0140831 | A1 | 5/2018 | Feldman et al. |
| 2018/0140843 | A1* | 5/2018 | Kent ..................... A61N 1/025 |
| 2018/0228391 | A1 | 8/2018 | Parker et al. |
| 2018/0228547 | A1 | 8/2018 | Parker et al. |
| 2018/0256052 | A1 | 9/2018 | Parker et al. |
| 2018/0289967 | A1 | 10/2018 | Bokil |
| 2019/0099602 | A1 | 4/2019 | Esteller et al. |
| 2019/0175915 | A1 | 6/2019 | Brill et al. |
| 2019/0209844 | A1 | 7/2019 | Esteller et al. |

(56) References Cited

U.S. PATENT DOCUMENTS

| | | |
|---|---|---|
| 2019/0275331 A1 | 9/2019 | Zhu |
| 2019/0290900 A1 | 9/2019 | Esteller et al. |
| 2019/0298992 A1 | 10/2019 | Zhang et al. |
| 2019/0299006 A1 | 10/2019 | Marnfeldt |
| 2019/0366094 A1 | 12/2019 | Esteller et al. |
| 2020/0155019 A1 | 5/2020 | Esteller et al. |
| 2020/0305745 A1 | 10/2020 | Wagenbach et al. |
| 2020/0376263 A1 | 12/2020 | Zhu |
| 2021/0023374 A1 | 1/2021 | Block et al. |

FOREIGN PATENT DOCUMENTS

| | | |
|---|---|---|
| WO | 2012/155186 | 11/2012 |
| WO | 2015/077362 | 5/2015 |
| WO | 2017/100866 | 6/2017 |
| WO | 2017/173493 | 10/2017 |
| WO | 2017/210352 | 12/2017 |
| WO | 2017/219096 | 12/2017 |
| WO | 2021/021659 | 2/2021 |

OTHER PUBLICATIONS

International Search Report and Written Opinion for PCT Application No. PCT/US2020/038811 dated Nov. 4, 2020.

\* cited by examiner

METHODS AND SYSTEMS FOR INTERLEAVING WAVEFORMS FOR ELECTRICAL STIMULATION AND MEASUREMENT

CROSS-REFERENCE TO RELATED APPLICATIONS

This application claims the benefit under 35 U.S.C. § 119(e) of U.S. Provisional Patent Application Ser. No. 62/864,195, filed Jun. 20, 2019, which is incorporated herein by reference.

FIELD

The present disclosure is directed to the area of implantable electrical stimulation systems and methods of making and using the systems. The present disclosure is also directed to methods and systems for interleaving waveforms to provide electrical stimulation and measurement.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Deep brain stimulation can be used to treat a variety of diseases and disorders.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is an electrical stimulation system that includes at least one electrical stimulation lead, each of the at least one electrical stimulation lead including a plurality of stimulation electrodes; and a processor coupled to the lead and configured to perform actions. The actions include directing delivery of at least one therapeutic waveform through at least one of the stimulation electrodes of the at least one electrical stimulation lead to tissue of a patient during each of a plurality of therapeutic periods; and directing sensing of an electrical signal using at least one of the stimulation electrodes of the at least one electrical stimulation lead during each of a plurality of sensing periods, wherein the therapeutic periods alternate with the sensing periods.

In at least some aspects, directing sensing includes, during at least one of the sensing periods, directing the sensing of the electrical signal without delivering a waveform through the stimulation electrodes.

In at least some aspects, directing sensing includes directing delivery of at least one sensing waveform through at least one of the stimulation electrodes of the at least one electrical stimulation lead during at least one of the sensing periods. In at least some aspects, parameters for the sensing waveform differ from parameters for the therapeutic waveform. In at least some aspects, directing delivery of at least one sensing waveform includes, for a set of consecutive sensing periods, directing delivery of the at least one sensing waveform from a different at least one electrode during each one of the sensing periods of the set. In at least some aspects, the sensing waveform is a biphasic waveform including a positive phase and a negative phase. In at least some aspects, the therapeutic waveform is a biphasic waveform comprising a positive phase and a negative phase and directing delivery of at least one therapeutic waveform and directing delivery of at least one sensing waveform comprises, for a pair of consecutive therapeutic and sensing periods, directing delivery of the therapeutic waveform during the therapeutic period with a first temporal order of the positive and negative phases of the therapeutic waveform and directing delivery of the sensing waveform during the sensing period with a second temporal order of the positive and negative phases of the sensing waveform that is opposite the first temporal order.

In at least some aspects, an amplitude of the sensing waveform is larger than an amplitude of the therapeutic waveform and a pulse width of the sensing waveform is shorter than a pulse width of the therapeutic waveform. In at least some aspects, the therapeutic periods are longer or shorter in time than the sensing periods.

Another aspect is an electrical stimulation system that includes at least one electrical stimulation lead, each of the at least one electrical stimulation lead including a plurality of stimulation electrodes; and a processor coupled to the lead and configured to perform actions, including: directing delivery of a first biphasic waveform through at least one of the stimulation electrodes of the at least one electrical stimulation lead to tissue of a patient, wherein the first biphasic waveform includes a first phase and a second phase which occurs after the first phase and is opposite in polarity to the first phase; directing sensing of a first electrical signal using at least one of the stimulation electrodes of the at least one electrical stimulation lead after delivery of the first biphasic waveform; after directing delivery of the first biphasic waveform, directing delivery of a second biphasic waveform through at least one of the stimulation electrodes of the at least one electrical stimulation lead to tissue of the patient, wherein the second biphasic waveform includes a third phase and a fourth phase which occurs after the third phase, wherein the third phase is opposite in polarity to both the first phase and the fourth phase; directing sensing of a second electrical signal using at least one of the stimulation electrodes of the at least one electrical stimulation lead after delivery of the second biphasic waveform; and combining the first and second electrical signals to reduce at least one artifact arising in the sensing of the first and second electrical signals.

In at least some aspects, the first and second biphasic waveforms are therapeutic waveforms. In at least some aspects, the first biphasic waveform is asymmetric. In at least some aspects, the first and second biphasic waveforms are the same except for temporal phase ordering. In at least some aspects, the actions further include scaling at least one of the first and second electrical signals prior to combining the first and second electrical signals. In at least some aspects, combining the first and second electrical signals includes adding or averaging the first and second electrical signals.

Yet another aspect is an electrical stimulation system that includes at least one electrical stimulation lead, each of the at least one electrical stimulation lead including a plurality of stimulation electrodes; and a processor coupled to the lead and configured to perform actions, including: a) directing delivery of a first waveform through at least one of the stimulation electrodes of the at least one electrical stimulation lead to tissue of a patient; b) directing sensing of a first electrical signal from the tissue using at least one of the stimulation electrodes of the at least one electrical stimulation lead after delivery of the first waveform; c) after directing delivery of the first waveform, directing delivery of a second waveform through at least one of the stimulation electrodes of the at least one electrical stimulation lead to tissue of the patient, wherein the first waveform differs from the second waveform in amplitude, pulse shape, pulse width, pulse period, electrode selection, or electrode fractionalization; d) directing sensing of a second electrical signal from the tissue using at least one of the stimulation electrodes of the at least one electrical stimulation lead after delivery of the second waveform; and e) using the first and second electrical signals to adjust at least one of the first waveform or the second waveform.

In at least some aspects, the first and second waveforms are therapeutic waveforms. In at least some aspects, the actions further include, after directing delivery of the first and second waveforms, directing delivery of a third waveform through at least one of the stimulation electrodes of the at least one electrical stimulation lead to tissue of the patient, wherein the third waveform differs from the first and second waveforms in amplitude, pulse shape, pulse width, pulse period, electrode selection, or electrode fractionalization; and directing sensing of a third electrical signal from the tissue using at least one of the stimulation electrodes of the at least one electrical stimulation lead after delivery of the third waveform.

In at least some aspects, the first and second waveforms are biphasic waveforms with a positive phase and a negative phase. In at least some aspects, the actions further include repeating steps a) to d) except reversing a temporal order of the positive phase and negative phase of the first and second waveforms.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of implantable electrical stimulation systems and methods of making and using the systems. The present disclosure is also directed to methods and systems for interleaving waveforms to provide electrical stimulation and measurement.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated herein by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, or peripheral nerve stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for spinal cord stimulation, but it will be understood that any of the leads can be used for applications other than spinal cord stimulation, including deep brain stimulation, peripheral nerve stimulation, dorsal root ganglion stimulation, sacral nerve stimulation, or stimulation of other nerves, muscles, and tissues.

Figure 1:
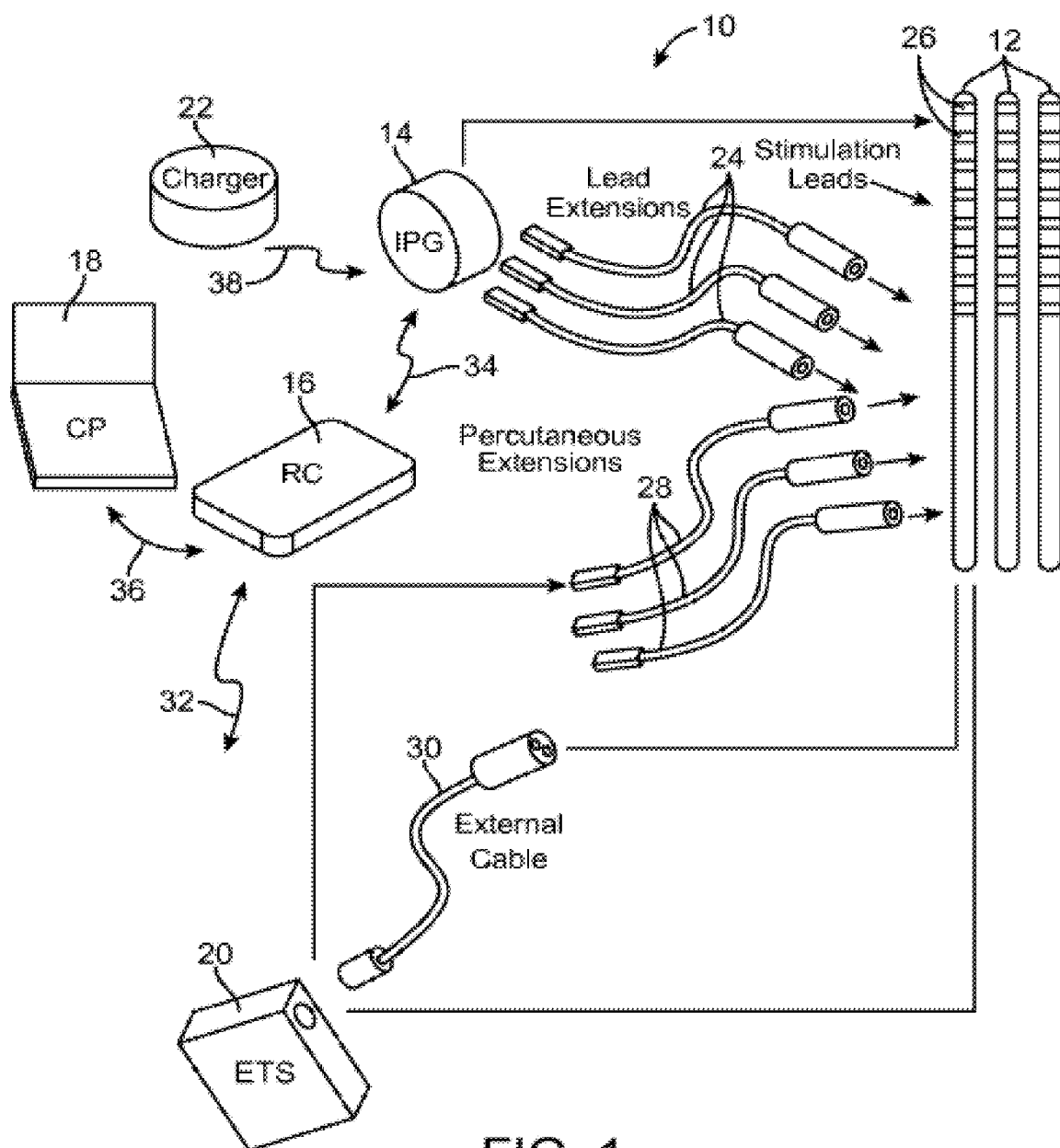
FIG. 1 is a schematic view of one embodiment of an electrical stimulation system.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22. The IPG and ETS are examples of control modules for the electrical stimulation system.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity or at any other suitable site. The implantable pulse generator can have multiple stimulation channels which may be independently programmable to control the magnitude of the current stimulus from each channel. In some embodiments, the implantable pulse generator can have any suitable number of stimulation channels including, but not limited to, 4, 6, 8, 12, 16, 32, or more stimulation channels. The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programmed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated herein by reference.

Knowledge and characterization of physiological response to stimulation, as well as the local stimulation environment around a lead or the electrodes of a lead, can provide useful information. For example, information can be determined regarding the activity, activity intensity, posture, or postural position of the patient or changes in activity, activity intensity, posture, or postural position of the patient; impedance, conductivity, or capacitance of the tissue near the lead or electrodes; a stimulation induced voltage distribution or current intensity; tissue charging or discharging characteristics; changes in the heart beat or respiration of the patient; or any other suitable electrical characteristics of the tissue. Changes in the local stimulation environment may be used to indicate, infer or determine patient posture or activity; may indicate the development, presence, or alterations in scar tissue or fluid around the lead or electrode; may indicate thickness of the fat tissue, thickness of the cerebral spinal fluid (for spinal cord stimulation systems); may indicate lead position in spinal canal, relative lead position or electrode position among multiple lead array; or the like or any combination thereof.

As described herein, electrodes of the lead(s) can be used to sense local electrical characteristics of the environment around the lead(s) and electrodes during and between electrical pulses or waveforms (which can be, for example, therapeutic stimulation pulses or waveforms, sub-perception pulses or waveforms, sensing pulses or waveforms, or other electrical pulses or waveforms). Sensing will be exemplified herein by the measurement of electrophysiological signals, such as ESG (electrospinogram) signals, received or detected at the electrode(s) used for sensing. It will be understood that electrical characteristics, such as electric field potential, current, resistance, or impedance, can be measured in addition to, or as an alternative to, the electrophysiological signals and that the description presented herein can be readily applied to these other electrical characteristics. It will also be understood that other electrophysiological signals, such as EEG (electroencephalogram), ECG (electrocardiogram), or EMG (electromyogram) signals can also be measured.

In addition to being dependent on the physical and electrical characteristics of the local tissue, the sensed signals can arise a variety of different electrical sources including, but not limited to, stimulation and other electrical pulses, evoked or spontaneous neural response, neural signals, heartbeat signals, respiration, patient activity (e.g., sleep, active, inactive, etc.), patient posture, and the like.

When sensing electrophysiological signals there may be difficulty extracting the physiological response from the sensed signals. This difficulty may arise for one or more reasons including, but not limited to, one or more of the following: 1) the physiological response may not be elicited by the therapeutic stimulation parameters (for example, the stimulation may be at low sub-perception levels that may not always elicit and evoked neural response); 2) the stimulation pulse width may overlap with the neural response; or 3) the stimulation frequency may be sufficiently high that evoked neural responses are not always elicited or not visible. Moreover, stimulation artifacts can interfere with the sensed signals.

Figure 2:
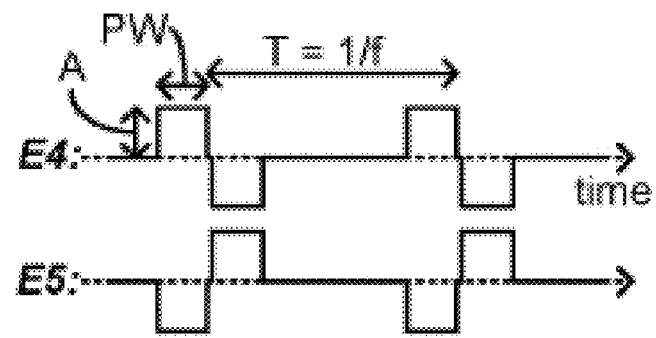
FIG. 2 is a schematic illustration of one embodiment of a biphasic electrical pulse using electrodes E4 and E5.

FIG. 2 illustrates an example of stimulation pulses according to a particular stimulation program and as executable by the IPG or ETS 70. In this example, stimulation is provided by electrodes 4 and 5 (E4 and E5) of a lead and each stimulation waveform is biphasic, meaning that a first phase is quickly followed by an opposite polarity second phase. The pulse width (PW) can be the duration of either of the phases individually as shown, or can be the entire duration of the biphasic waveform including both phases (which may also be considered the period of the waveform). The frequency (f) and amplitude (A) of the waveform is also shown in FIG. 2. Although not shown, monophasic waveforms—having only a first phase but not followed by an active-charge recovery second phase—can also be used. In addition, biphasic waveforms where the second phase is passive charge recovery are also useful. Multiphasic waveforms (e.g., triphasic and so forth) can be used.

At least some biphasic waveforms are useful because the second phase can actively recover any charge build up after the first phase residing on capacitances (such as the DC-blocking capacitors in the IPG or ETS) in the current paths between the active electrodes. In the example stimulation program shown in FIG. 2, electrode E4 is selected as the anode electrode while electrode E5 is selected as the cathode electrode (during the first pulse phase). Because two electrodes 16 are used, this represents bipolar stimulation. The pulses as shown are pulses of constant current and the amplitude of the current at any point in time is equal but opposite such that current injected into the patient's tissue by one electrode (e.g., E4) is removed from the tissue by the other electrode (E5). The area of the first and second phases are equal, providing active charge recovery of the same amount of charge during each phase. Although not shown, more than two electrodes can be active at any given time to produce multipolar stimulation. For example, electrode E4 could comprise an anode providing a +10 mA current pulse amplitude, while electrodes E3 and E5 could both comprise cathodes with −7 mA and −3 mA current pulse amplitudes respectively. Monopolar stimulation can utilize one electrode on the lead and a second electrode that is distant from the lead, such as the case of the IPG or an external electrode.

Figure 3A:
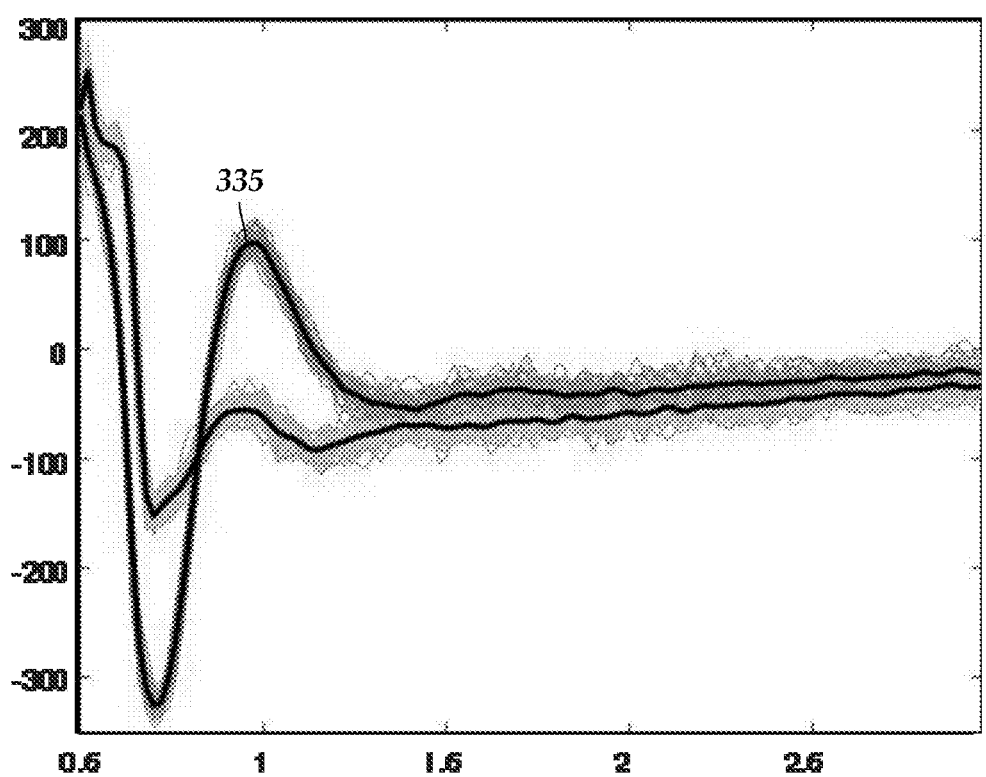
FIG. 3A is a schematic illustration of one embodiment of a neural response or neural signal.
Figure 3B:
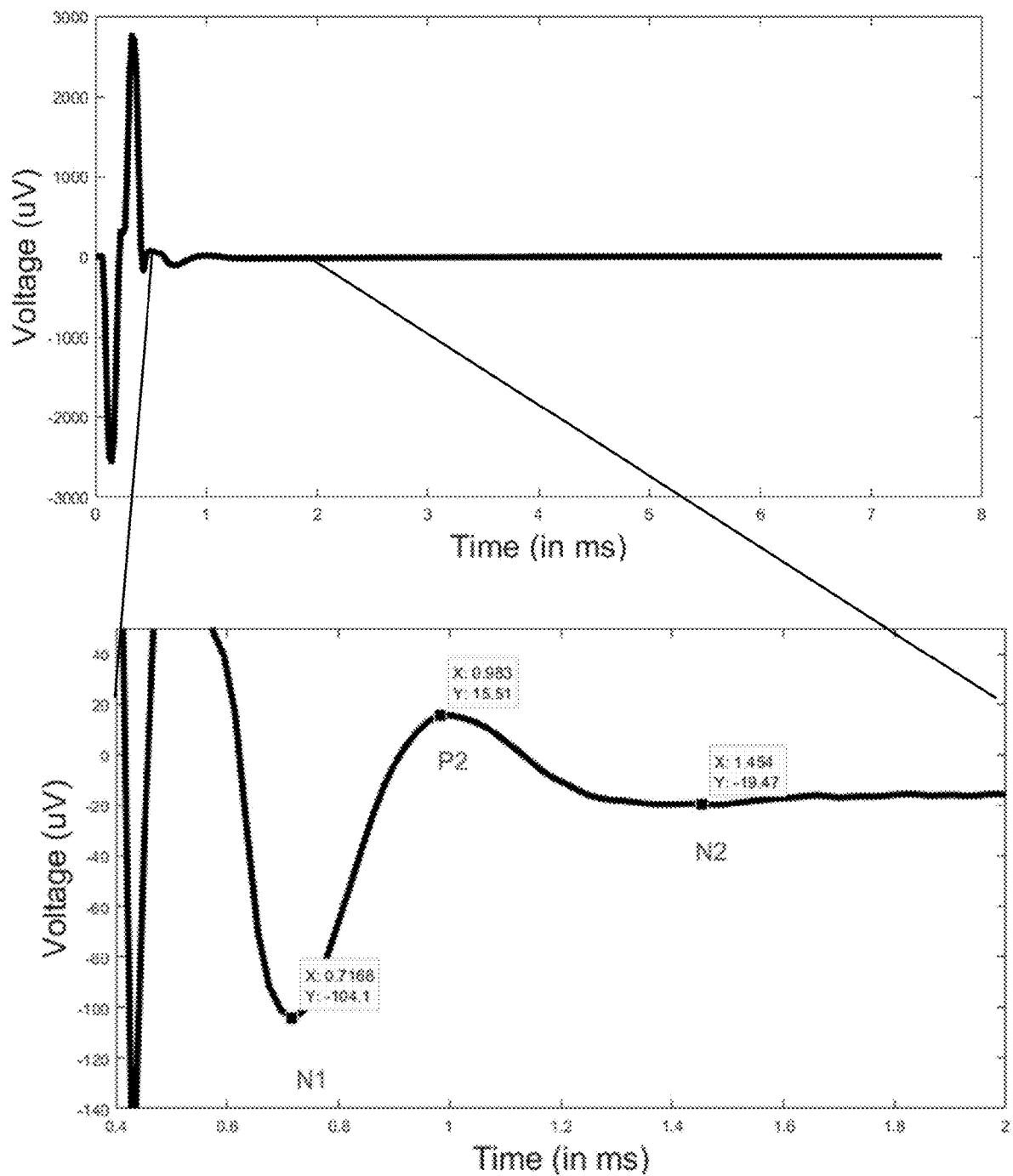
FIGS. 3B and 3C are graphs of an evoked composite action potential (ECAP) and also illustrate an artifact arising from a stimulation induced field potential.
Figure 3C:
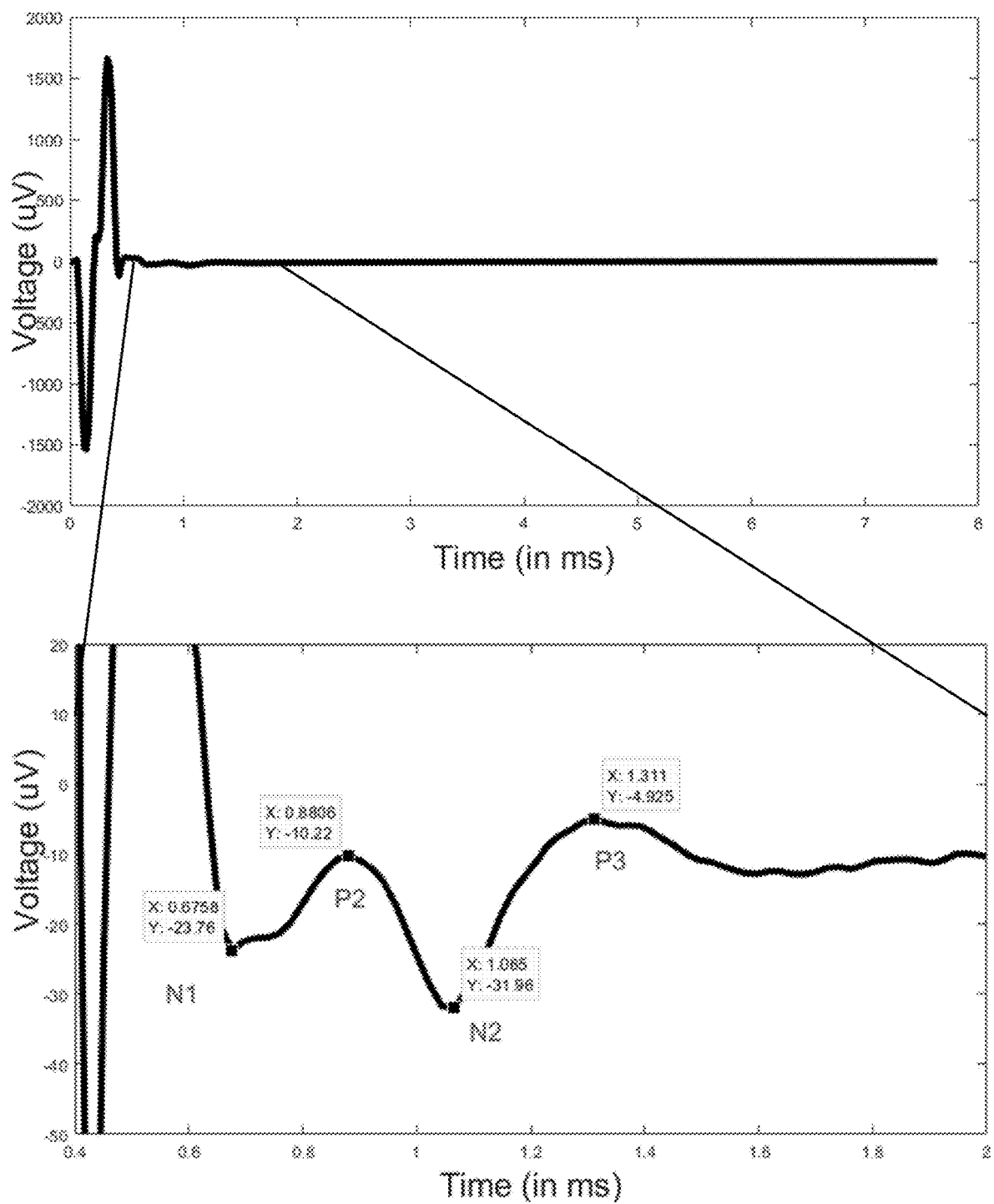

FIG. A3 illustrates one example of a neural response 335 or neural signal. When a neural fiber is recruited by electrical stimulation, it will issue an action potential—that is, the neural fiber will "fire." Should recruitment from electrical stimulation cause the neural fiber's resting state the neural fiber will depolarize, repolarize, and hyperpolarize before coming to rest again. If electrical stimulation continues, the neural fiber will fire again at some later time. FIGS. 3B and 3C illustrate one examples of an evoked compound action potential (ECAP) which can be a cumulative response of neural fibers recruited and firing within a volume, as well as an artifact arising from a stimulation induced field potential. An ECAP's shape can be a function of the number and types of neural fibers that are recruited. The stimulation current was 4.6 mA in FIG. 3B and 2.8 mA in FIG. 3C.

Interleaving therapeutic and sensing periods can alleviate difficulties in sensing an electrophysiological response after the stimulation. Interleaving therapeutic and sensing periods can also be applied for sensing non-neural signals, such as artifacts arising from the applied waveform(s), or for sensing spontaneous neural signals or local field potentials.

Figure 4A:
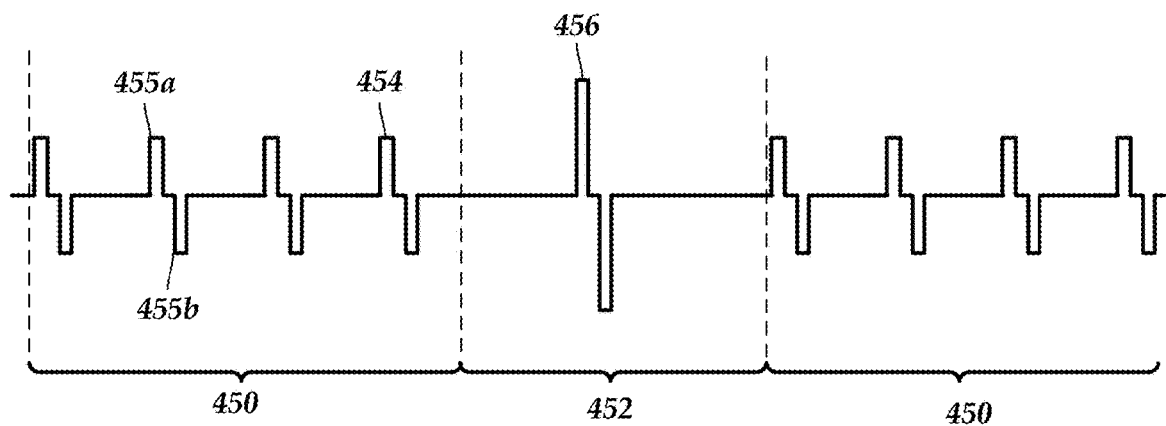
FIG. 4A is a schematic representation of one embodiment of a waveform sequence utilizing alternating therapeutic periods and sensing periods.
Figure 4B:
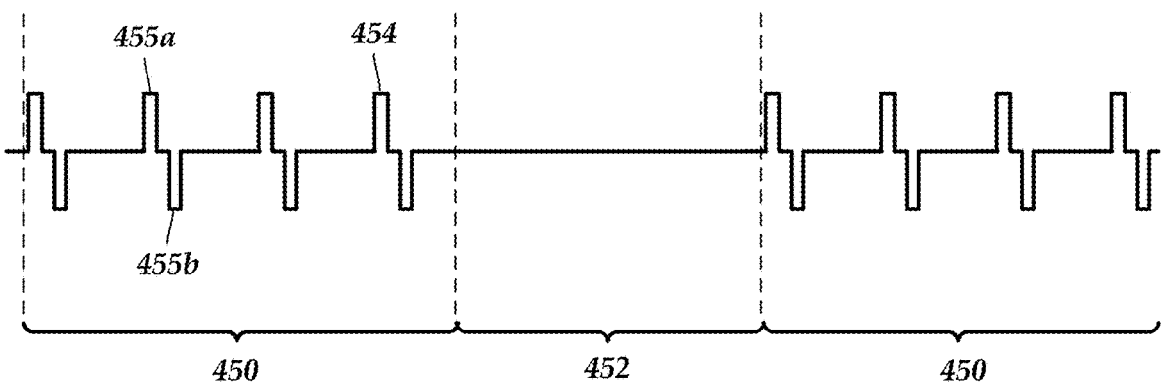
FIG. 4B is a schematic representation of another embodiment of a waveform sequence utilizing alternating therapeutic periods and sensing periods.

FIGS. 4A and 4B illustrate two examples of the temporal interleaving of therapeutic periods 450 and sensing periods 452. As illustrated, the sensing periods 452 and therapeutic periods 450 alternate in a graph of time versus current. The length of time of the sensing periods 452 may be equal to, shorter than, or longer than the length of time of the therapeutic periods 450. As an example, the therapeutic periods may have a length of 100 to 200 ms and the sensing period a length of 20 msec. It will be recognized that the length of the time of the sensing periods 452 can be uniform or can vary between sensing periods. Similarly, the length of time of the therapeutic periods 450 can be uniform or can vary between therapeutic periods.

The therapeutic stimulation during the therapeutic periods 450 can be provided using any suitable therapeutic waveform 454 or combination of waveforms. In FIGS. 4A and 4B, the therapeutic waveform 454 is a repeated biphasic waveform with a positive phase 455a and a negative phase 455b. In the illustrated example, the therapeutic period includes four biphasic waveforms 454, but it will be recognized that other embodiments can include therapeutic periods with any suitable number of waveforms and that the number of waveforms per therapeutic period can be uniform or can vary between therapeutic periods.

The therapeutic waveform 454 can be, for example, a tonic pulse waveform providing stimulation at any suitable frequency (for example, in range from 1 Hz and 2 kHz); a burst waveform with any suitable inter-burst frequency (for example, in a range from 1 Hz to 2 kHz) with a higher intra-burst frequency (for example in a range from 100 Hz to 5, 10, 25, or 50 kHz) with two, three, four, five, six, or more pulses per burst; a sinewave; a modulated waveform; a sub-perception waveform (in which the stimulation is not perceived by the patient); or any other suitable waveform (utilizing any other suitable shape) or any combination of waveforms. Examples of some suitable waveforms are disclosed in U.S. Patent Application Publication No. 2017/0157410, incorporated herein by reference.

The therapeutic waveform 454 is delivered using one or more electrodes 26 of a lead 12 (FIG. 1) or a combination of leads. The therapeutic waveform 454 can be bipolar (using two electrodes of the lead(s)), multipolar (using three or more electrodes of the lead(s)), or monopolar (using a single electrode of the lead(s) with a second electrode that is distant from the leads, such as the case of the IPG 14 or an external electrode disposed on the patient.)

In FIG. 4A, a sensing waveform 456 can be used to elicit neural response during the sensing period 452. The sensing waveform 456 can be any suitable waveform and can be delivered using monopolar, bipolar, or multipolar (using, respectively, one, two, or three or more of the electrodes 26 of one or more of the leads 12 (FIG. 1).) In the illustrated embodiment of FIG. 4A, the sensing waveform 456 is a single biphasic waveform that is temporally separated from the therapeutic waveform 454. The sensing waveform 456 can include an active or passive recharge pulse Any other suitable waveform, or combination of waveforms, can be used as the sensing waveform 456 including, but not limited to, a short train of pulses with predefined fixed parameters that produce a neural response. In at least some embodiments, the sensing waveform can utilize the same parameters (for example, amplitude and pulse width) as the therapeutic waveform. In other embodiments, the sensing waveform uses one or more parameters (for example, amplitude, pulse shape, pulse width, pulse period, electrode selection, or electrode fractionalization) that are different in value from the therapeutic waveform. For example, the sensing waveform may utilize a larger amplitude, but shorter pulse width, as compared to the therapeutic waveform, as illustrated in FIG. 4A. In at least some embodiments, the sensing waveform can have a different shape from the therapeutic waveform (for example, a sinewave or other shape) or may be delivered using different electrode(s) or different electrode fractionalizations (i.e., the fraction of total current or voltage on each of the selected electrodes).

As another example, to enhance sensing of an artifact signal (arising, for example, from the therapeutic or sensing waveform, the sensing waveform can have a smaller amplitude than the therapeutic waveform to prevent the sensed artifact voltage from railing (i.e., saturating at the top). This artifact sensing period could also be alternated with sensing periods that utilize a sensing waveform to sensing the evoked neural response or other electrophysiological signal. In at least some embodiments, a closed loop system can utilize this arrangement to obtain information from sensed evoked signals and sensed artifact signals that can then be used to adjust the therapeutic periods or therapeutic waveform.

As illustrated in FIG. 4A, the sensing waveform delivered during the sensing period is interleaved with the therapeutic waveforms delivered during the therapeutic period. In at least some embodiments, the patient may not feel or perceive the sensing waveform. For example, the sensing waveform may have a relatively short pulse width with a high amplitude that is not perceptible to the patient. In at least some embodiments, the sensing waveform will not affect the therapeutic stimulation.

In other embodiments, the sensing waveform may also be a therapeutic waveform, but with properties that facilitate sensing. In at least some embodiments, the patient may perceive the sensing waveform and therefore the electrodes used in the sensing waveform may be chosen such that the perception is located in an agreeable area for the patient (e.g., within the pain topography, or other agreeable area). In at least some embodiments, because the patient perceives the sensing waveform, instances of the sensing waveform may be presented at irregular intervals in accordance with a pattern that the patient deems agreeable or particularly pleasant, or even therapeutic.

The sensing waveform 456 facilitates physiological sensing such as, for example, sensing an ESG (electrospinogram) signal. The system (for example a control module, such as an implantable pulse generator (IPG) or external trial stimulation (ETS); remote control (RC); clinician programmer (CP); or other device) may use the sensed signals from the tissue to, for example, determine information about posture; determine changes in the sensed signals that the systems can use to tune or adjust a stimulation parameter; or for any other suitable purpose or combination of purposes. In at least some embodiments, the sensing waveform may be selected to reduce or minimize artifact contamination in the sensed physiological signal or ESG and may facilitate feature extraction or pattern recognition of specific attributes of the sensed signal.

In at least some embodiments, the sensing waveform 456 is delivered from the same electrode(s) during each sensing period 452. In at least some embodiments, the sensing waveform 456 in each successive sensing period 452 can be delivered using electrodes that are proximal to, or distal to, the electrodes used to deliver the sensing waveform in the preceding period. In the case of spinal cord stimulation, the spatially interleaved sensing waveforms 456 can sense, for example, how the distance between the spinal cord and lead changes at different vertebral levels. In at least some embodiments, the arranged sequence of sensing waveforms can be selected and timed so that a sensing period 452 for each electrode or set of electrodes along the lead can occur in a time period that is shorter than the posture or activity of the patient can adjust. For example, for an eight electrode lead, the combination of a sensing period and adjacent therapeutic period can be in the range of 5 to 10 ms, resulting in a total period for all sensing at all eight electrodes of 40 to 80 msec.

In contrast, in FIG. 4B, there is no sensing waveform during the sensing period 452. The absence of a sensing waveform in the sensing period 452 allows the sensing or measurement of the ESG in response to the previous therapeutic period 450.

Figure 5:
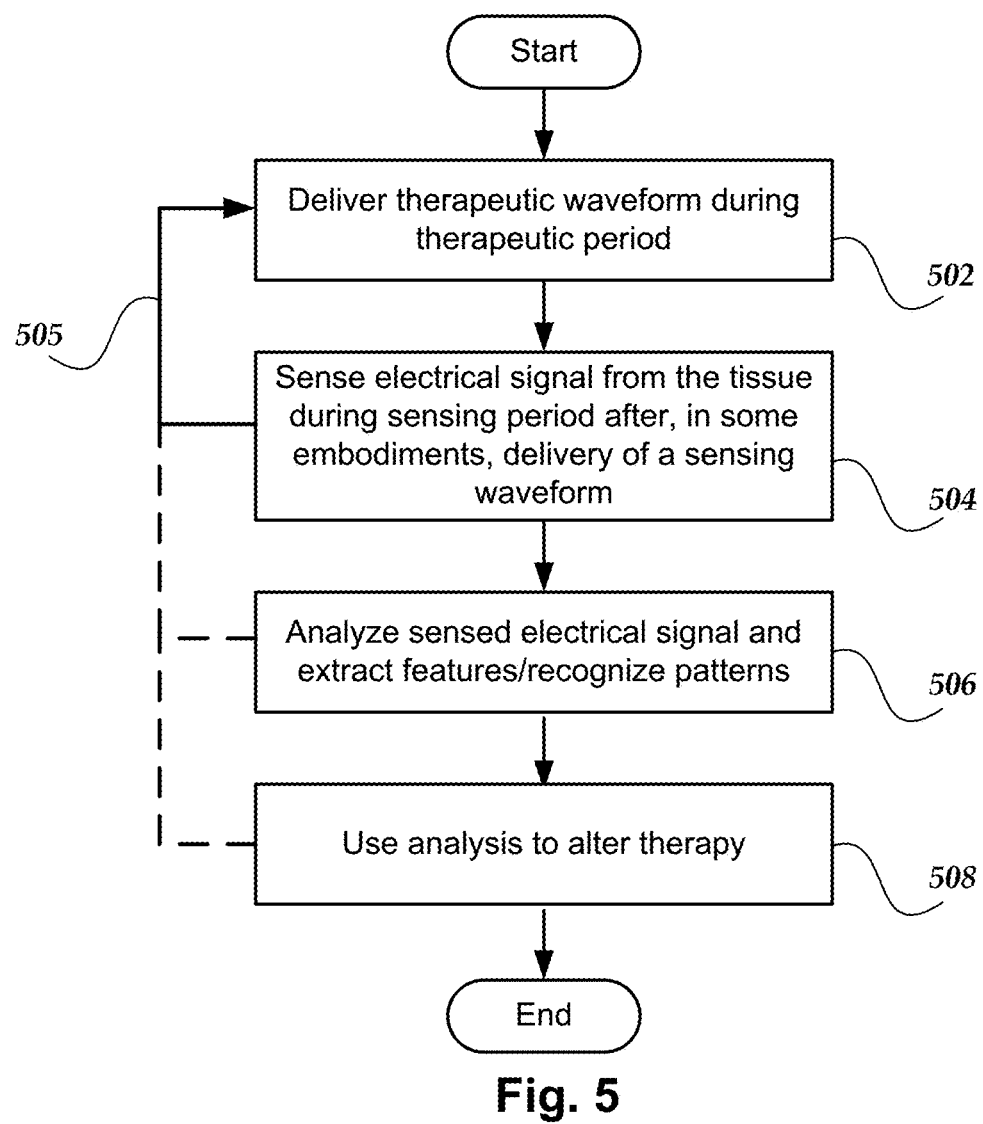
FIG. 5 is a flowchart of one method of stimulating and seeing using electrodes on one or more leads and utilizing alternating therapeutic periods and sensing periods.

The embodiments in FIGS. 4A and 4B illustrate examples of a method of stimulating and sensing using electrodes on one or more leads. FIG. 5 is a flowchart of one embodiment of a method of stimulating and sensing using electrodes on one or more leads. The sequences of waveforms illustrated in FIGS. 4A and 4B are examples of the waveforms and arrangements that can be used in the method of FIG. 5.

In step 502, at least one therapeutic waveform is delivered using the electrodes of the lead(s) during a therapeutic period. As described above with respect to the sequences illustrated in FIGS. 4A and 4B, the therapeutic waveform can be monophasic, biphasic, or multiphasic and can be monopolar, bipolar, or multipolar. The therapeutic period can include one or more of the therapeutic waveforms.

In step 504, after the therapeutic period and, in some embodiments, after delivery of a sensing waveform 456 (FIG. 4A), an electrical signal, such as a neural response; a spontaneous neural signal; an ECAP; a ECG, ESG, EEG, or EMG signal; an electric field potential; or any other suitable signal or combination of signals, is sensed during a sensing period. FIG. 4A illustrates a sensing period 452 that includes a sensing waveform 456 and FIG. 4B illustrates a sensing period 452 without a sensing waveform. In at least some embodiments, the sensing is performed using two electrodes of the lead(s), but it will be understood that an electrode not on the lead can also be used in combination with an electrode on a lead.

In step 506, the sensed electrical signal from step 504 is analyzed to produce information about the patient or tissue, extract features from the sensed electrical signal, recognize patterns in the sensed electrical signal, or the like. The analysis of the sensed electrical signal may include information about neural response, evoked or spontaneous neural signals, heartbeat signals, respiration, patient activity (e.g., sleep, active, inactive, coughing, laughing, and so forth), patient posture, and the like.

In optional step 508, the analysis of step 506 may be used to alter the stimulation therapy. For example, stimulation parameters may be altered due to changes in patient posture or activity as indicated in the sensed electrical signal.

As indicated by the lines 505, any combination of steps 502, 504, 506, and 508 can be repeated with the therapeutic periods and sensing periods alternating.

Figure 6:
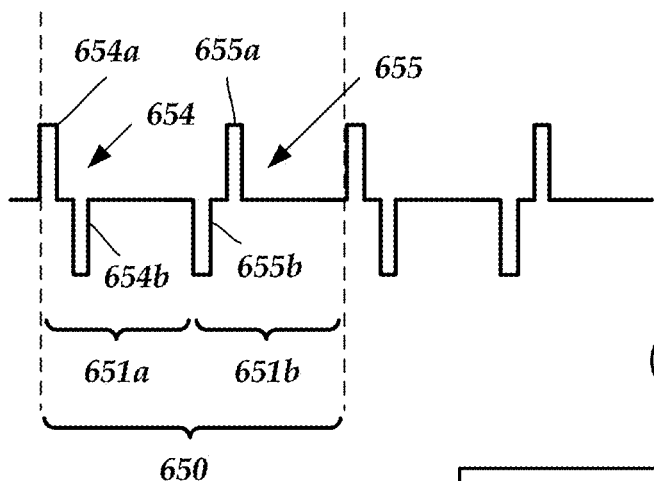
FIG. 6 is a schematic representation of one embodiment of a sequence of biphasic waveforms with alternating temporal order of the phases of the waveform.

The therapeutic waveform can generate artifacts in the resulting sensed signal. FIG. 6 illustrates one embodiment of a sequence of biphasic therapeutic waveforms that can reduce or eliminate artifacts in a sensed signal that arise from the biphasic therapeutic waveforms. As illustrated in FIG. 6, a first waveform 654, with a positive phase 654a followed by a negative phase 654b, is interleaved with a second waveform 655, with a negative phase 655b followed by a positive phase 655a, to form a stimulation block 650 with a first stimulation epoch 651a containing the first waveform and a second stimulation epoch 651b containing the second waveform. This interleaving of two biphasic waveforms 654, 655 with opposite temporal ordering of the phases can reduce or eliminate artifact contamination in the sensed signal (such as an ESG or a sensed evoked neural response to the stimulation) and may facilitate feature extraction of specific attributes.

The therapeutic waveforms in FIG. 6 alternate the polarity order of the waveform phases so that at least some artifacts arising from the first waveform 654 and the second waveform 655 exhibit opposite polarities. In contrast, the neural responses will have the same polarity (see, FIG. 3).

In at least some embodiments, the artifacts arising from the waveforms 654, 655 can be reduced or eliminated by adding, averaging, or otherwise combining the sensed signals from the first and second stimulation epochs 651a, 651b. In at least some embodiments, the sensed signals from the first and second stimulation epochs 651a, 651b can be scaled based on the size of the artifacts in the respective sensed signals or based on the size of the neural response in the sensed signals or based on any other suitable features in the sensed signals. In at least some of these embodiments, the scaled sensed signals can be added, averaged, or otherwise combined.

In at least some embodiments, the phases 654a, 654b, 655a, 655b of each of the waveforms 654, 655 can be symmetric except for polarity (for example, having the same amplitude and width), as illustrated in FIG. 6, or can be asymmetric with different amplitude, width, or other parameter or any combination of parameters. In at least some embodiments the first and second waveforms 654, 655 can be symmetric except for the temporal arrangement of the two phases, as illustrated in FIG. 6, or can be asymmetric with different amplitudes, widths, or other parameters or any combination of parameters.

In at least some embodiments, the arrangements of FIGS. 4A/4B and FIG. 6 can be combined to provide in sequence: 1) a first therapeutic period (similar to period 450 of FIGS. 4A/4B) during which one or more of the first waveforms 654 are delivered, 2) a first sensing period (similar to period 452 of FIGS. 4A/4B), 3) a second therapeutic period (similar to period 450 of FIGS. 4A/4B) during which one or more of the second waveforms 655 are delivered, and 4) a second sensing period (similar to period 452 of FIGS. 4A/4B). The sensed signals from the first and second sensing periods can be scaled, added, averaged, or otherwise combined as discussed above with respect to the first and second stimulation epochs 651a, 651b. In at least some embodiments, the entire period of time for the two therapeutic periods and two sensing periods can be arranged so that there is little or no change in patient status during that time period so that the signals between the two sensing periods represent the same patient state. For example, either period of time may be no more than 1 second or 500, 200, 100, or 50 milliseconds or less.

In another combination of the arrangements of FIG. 4A and FIG. 6, the waveforms 654, 655 of FIG. 6 can be used during the sensing periods 452 of FIG. 4A instead of the waveform 456.

Figure 7:
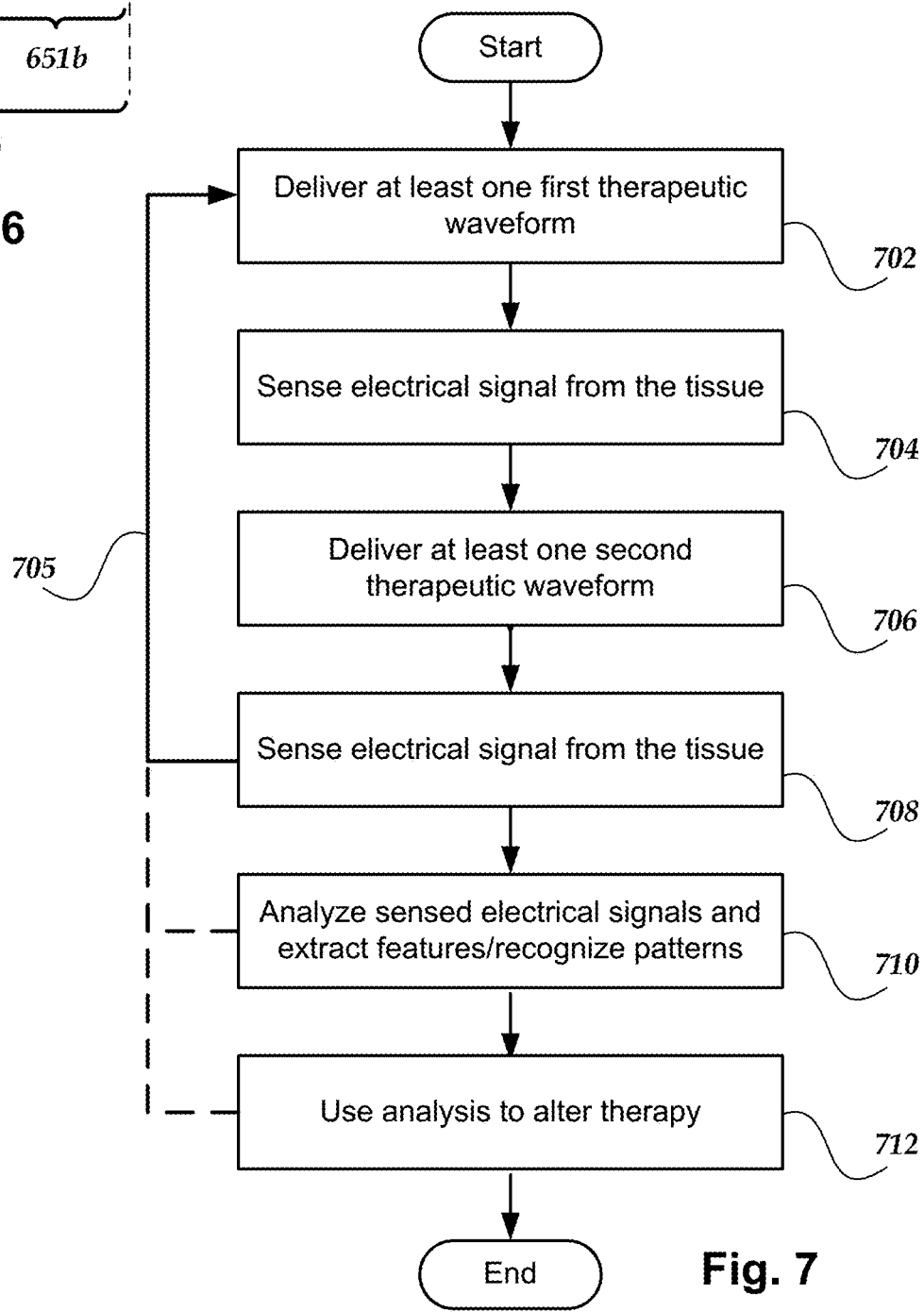
FIG. 7 is a flowchart of one method of stimulating and seeing using electrodes on one or more leads and utilizing alternating temporal order of phases of a biphasic waveform.

FIG. 7 is a flowchart illustrating one embodiment of a method of stimulating and sensing using electrodes on one or more leads and alternating the temporal order of phases of biphasic therapeutic waveforms. In step 702, at least one first therapeutic waveform is delivered using the electrodes of the lead(s). The therapeutic waveform is biphasic with a first phase and a second phase where the second phase is opposite in polarity to the first phase.

In step 704, an electrical signal, such as an electrospinogram signal or an electric field potential, is sensed after (and, optionally, before or during) delivery of the at least one first therapeutic waveform. In many instances, the sensing will be performed using two electrodes of the lead(s), but it will be understood that an electrode not on the lead can also be used in combination with an electrode on the lead.

In step 706, at least one second therapeutic waveform is delivered using the electrodes of the lead(s). The therapeutic waveform is biphasic with a third phase and a fourth phase where the third phase is opposite in polarity to the fourth phase and also opposite in polarity to the first phase of the at least one first therapeutic waveform.

In step 708, an electrical signal, such as an electrospinogram signal or an electric field potential, is sensed after (and, optionally, before or during) delivery of the at least one second therapeutic waveform. In many instances, the sensing will be performed using two electrodes of the lead(s), but it will be understood that an electrode not on the lead can also be used in combination with an electrode on the lead.

In step 710, the sensed electrical signals from steps 704 and 708 are analyzed. In at least some embodiments, the sensed electrical signals are scaled, added, averaged, or otherwise combined as described above in order to reduce or eliminate artifacts in the sensed electrical signals. The analysis of the sensed electrical signals can produce information, extract features from the sensed electrical signal, recognize patterns in the sensed electrical signals, or the like. The analysis of the sensed electrical signals may include information about neural response, neural signals, heartbeat signals, respiration, patient activity (e.g., sleep, active, inactive, etc.), patient posture, and the like.

In optional step 712, the analysis of step 710 may be used to alter the stimulation therapy. For example, stimulation parameters may be altered due to changes in patient posture or activity as indicated in the sensed electrical signals.

As indicated by arrow 705, any combination of steps 702, 704, 706, 708, 710, and 712 can be repeated with delivery of the first and second therapeutic waveforms alternating.

The adjustment of stimulation parameters based on sensing of signals can be enhanced by increasing the amount of information available from the sensing. This can be accomplished by, for example, using therapeutic waveforms or sensing waveforms with different parameters such as different amplitude, pulse shape, pulse width, pulse period, electrode selection, or electrode fractionalization. For example, the sensed responses to each of two consecutive therapeutic waveforms with different amplitudes, for example, 2 mA and 2.2 mA, can provide additional information, particularly when the therapeutic waveforms are delivered close in time so that there are no patient posture or activity changes during that period. The physiological response to two different therapeutic waveforms can provide more information, such as, for example, the current activity or posture, and may result in better adjustment of stimulation parameters to be delivered.

Figure 8A:
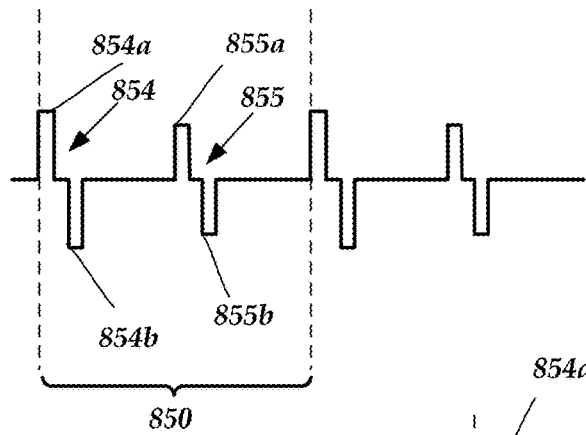
FIG. 8A is a schematic representation of one embodiment of a sequence of waveforms with different amplitudes.
Figure 8B:
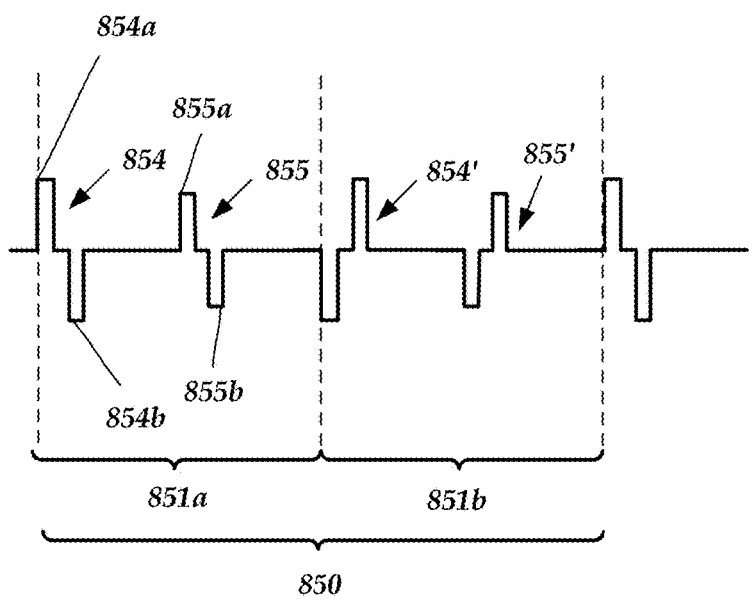
FIG. 8B is a schematic representation of another embodiment of a sequence of waveforms with different amplitudes.
Figure 8C:
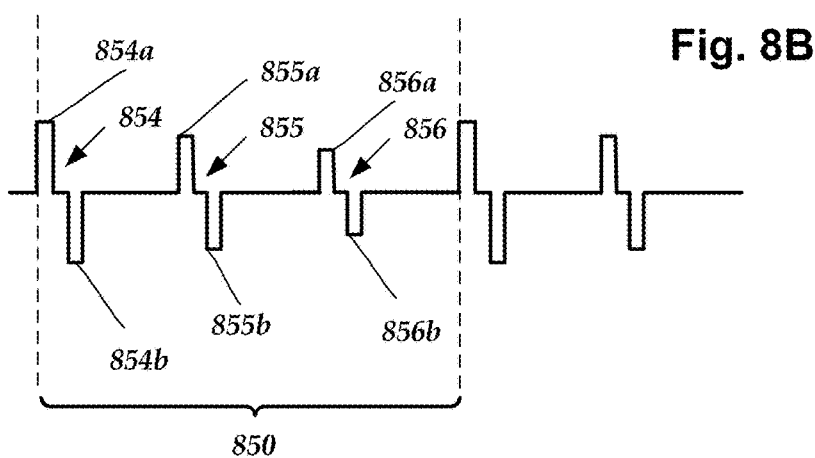
FIG. 8C is a schematic representation of a third embodiment of a sequence of waveforms with different amplitudes.

FIGS. 8A to 8C illustrate three embodiments of a sequence of biphasic therapeutic waveforms with two (FIGS. 8A and 8B) or three (FIG. 8C) waveforms with different amplitudes. In the illustrated embodiments, the amplitudes of the waveforms are different. It will be recognized that other waveform parameters, such as pulse width, can be selected instead of, or in addition to, amplitude for differing between waveforms.

As illustrated in FIG. 8A, a first waveform 854 having a first amplitude and a positive phase 854a followed by a negative phase 854b is interleaved with a second waveform 855 having a second, lower amplitude with a positive phase 855a followed by a negative phase 855b to form a stimulation block 850. This stimulation block 850 is repeated.

FIG. 8B illustrates a sequence that combines the concepts in FIG. 8A and FIG. 6 so that the first stimulation epoch 851a is the sequence of first and second waveforms 854, 855 illustrated in FIG. 8A and the second stimulation epoch 851b is the same sequence of waveforms except that the temporal order of the phases of the first and second waveforms 854', 855' is reversed. The two stimulation epochs 851a, 851b form a stimulation block 850 which is repeated. As described above, reversing the temporal order of the phases of the waveforms and combining the respective sensed signals can reduce or eliminate artifacts arising from the therapeutic waveforms.

FIG. 8C illustrates a sequence that includes the first and second waveforms 854, 855 of FIG. 8A and interleaves a third waveform 856 having a third amplitude and a positive phase 856a followed by a negative phase 856b to form the stimulation block 850. This stimulation block 850 is repeated. In one example, the first waveform has an amplitude of 1.0 mA, the second waveform has an amplitude of 1.2 mA, and the third waveform has an amplitude of 1.4 mA. It will be recognized that additional embodiments can include four, five, or more waveforms with each waveform having a different amplitude.

In at least some embodiments, the phases of each of the individual waveforms 854, 855, 857 can be symmetric except for polarity (for example, having the same amplitude and width), as illustrated in FIGS. 8A to 8C, or can be asymmetric with different amplitude, pulse shape, pulse width, pulse period, electrode selection, or electrode fractionalization, or other parameter or any combination of parameters.

In a combination of the arrangements of FIG. 4A and any one of FIGS. 8A to 8C, the waveforms 854, 855, 856 of any one of FIGS. 8A to 8C can be used during the sensing periods 452 of FIG. 4A instead of the waveform 456.

Instead of variation in amplitude, the different therapeutic waveforms can differ in electrode selection for delivery of the waveform to produce a spatial interleaving of the waveforms. For example, each successive waveform can be delivered using electrodes that are proximal to, or distal to, the electrodes used to deliver the preceding waveform. In the case of spinal cord stimulation, the spatially interleaved waveforms can sense, for example, how the distance between the spinal cord and lead changes at different vertebral levels. This spatial interleaving can also be combined with the arrangement of FIG. 4A so that each sensing period 452 includes one or more waveforms delivered from a different set of electrodes.

The therapeutic and sensing waveforms can differ in any of the following parameters: amplitude, pulse shape, pulse width, pulse period, electrode selection, or electrode fractionalization.

Figure 9:
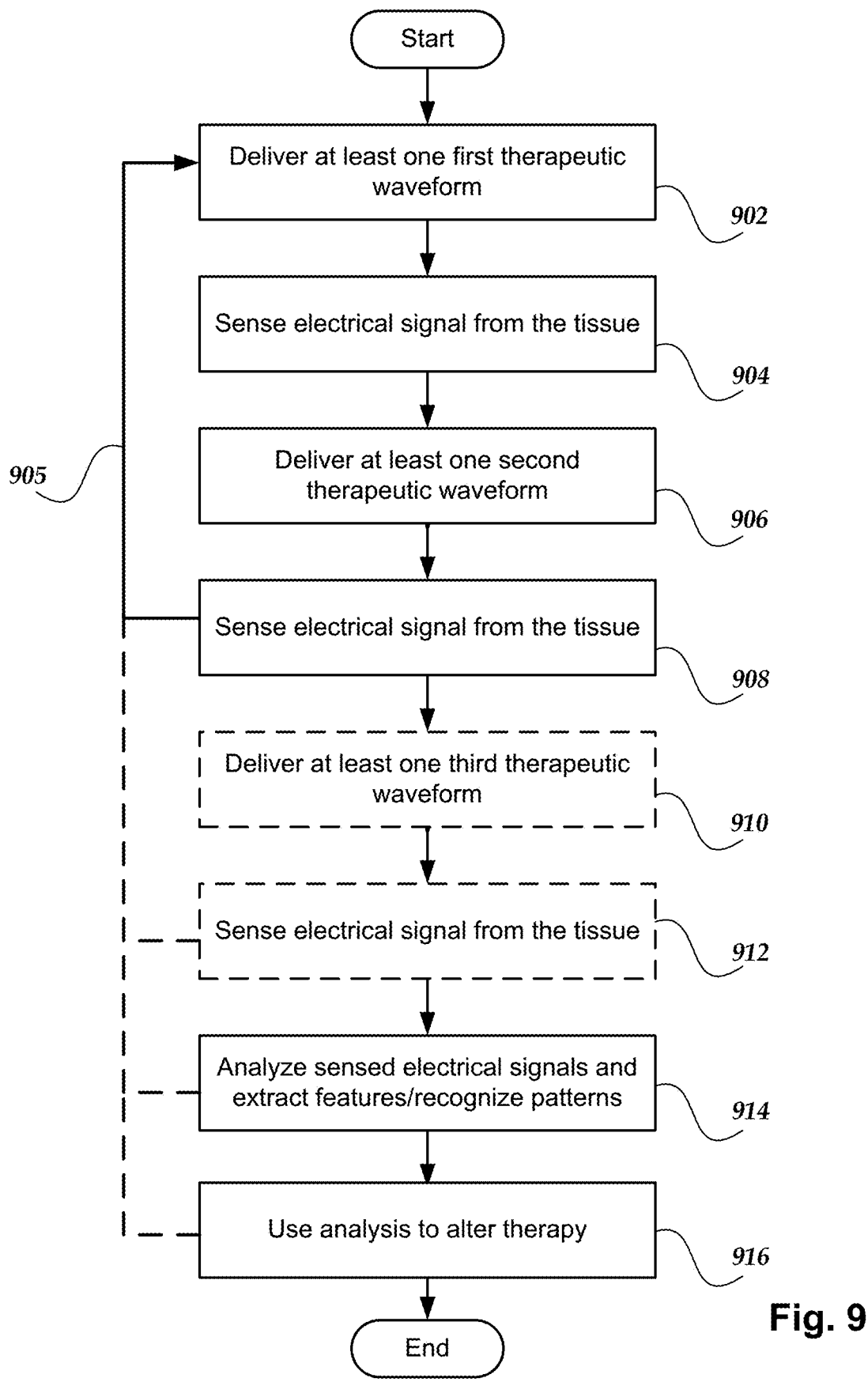
FIG. 9 is a flowchart of one method of stimulating and sensing using electrodes on one or more leads and waveforms with different amplitudes or other waveform parameters.

FIG. 9 is a flowchart illustrating one embodiment of a method of stimulating and sensing using electrodes on one or more leads and alternating the temporal order of phases of biphasic therapeutic waveforms. In step 902, at least one first therapeutic waveform is delivered using the electrodes of the lead. In step 904, an electrical signal, such as an electrospinogram signal or an electric field potential, is sensed after (and, optionally, before or during) delivery of the at least one first therapeutic waveform. In at least some embodiments, the sensing will be performed using two electrodes of the lead(s), but it will be understood that an electrode not on the lead can also be used in combination with an electrode on the lead.

In step 906, at least one second therapeutic waveform is delivered using the electrodes of the lead(s). The first and second therapeutic waveforms differ in at least one stimulation parameter, such as amplitude, pulse shape, pulse width, pulse period, electrode selection, or electrode fractionalization. In step 908, an electrical signal, such as an electrospinogram signal or an electric field potential, is sensed after (and, optionally, before or during) delivery of the at least one second therapeutic waveform. In at least some embodiments, the sensing will be performed using two electrodes of the lead(s), but it will be understood that an electrode not on the lead can also be used in combination with an electrode on the lead.

In optional step 910, at least one third therapeutic waveform is delivered using the electrodes of the lead(s). The first, second, and third therapeutic waveforms differ in at least one stimulation parameter, such as amplitude, pulse shape, pulse width, pulse period, electrode selection, or electrode fractionalization. In optional step 912, an electrical signal, such as an electrospinogram signal or an electric field potential, is sensed after (and, optionally, before or during) delivery of the at least one third therapeutic waveform. In at least some embodiments, the sensing will be performed using two electrodes of the lead(s), but it will be understood that an electrode not on the lead can also be used in combination with an electrode on the lead.

In step 914, the sensed electrical signals from steps 904, step 908, and optionally step 912 are analyzed. In at least some embodiments, the sensed electrical signals are scaled, added, averaged, or otherwise combined. The analysis of the sensed electrical signals can produce information, extract features from the sensed electrical signal, recognize patterns in the sensed electrical signals, or the like. The analysis of the sensed electrical signals may include information about neural response, neural signals, heartbeat signals, respiration, patient activity (e.g., sleep, active, inactive, etc.), patient posture, and the like.

In optional step 916, the analysis of step 914 may be used to alter the stimulation therapy. For example, stimulation parameters may be altered due to changes in patient posture or activity as indicated in the sensed electrical signals.

As indicated by arrow 905, any combination of steps 902, 904, 906, 908, 910, 912, 914, and 916 can be repeated with delivery of the first and second therapeutic waveforms alternating.

Figure 10:
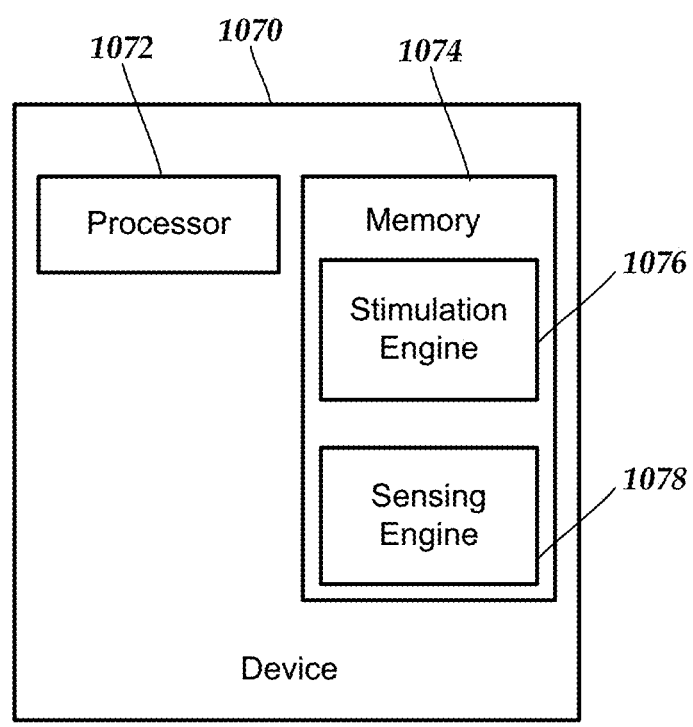
FIG. 10 is a schematic block diagram of a device with a processor and memory and a stimulation engine and sensing engine stored in the memory.

In at least some embodiments, the methods presented in the flowcharts of FIGS. 5, 7, and 9 (or any subset of the steps in those flowcharts) can be performed by a stimulation engine 1076 (or a stimulation module or stimulation algorithm) and a sensing engine 1078 (or a sensing module or sensing algorithm) residing in a memory 1074 and operating in a processor 1072 of a device 1070 as illustrated in FIG. 10. (In some embodiments, the stimulation engine 1076 and sensing engine 1078 can be combined into a stimulation/sensing engine.) The device 1070 can be, for example, devices illustrated in FIG. 1, such as an IPG 14, RC 16, CP 18, or ETS 20, or any other suitable device.

It will be understood that each block of the flowchart illustration, and combinations of blocks in the flowchart illustration and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computing device. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Figure 11:
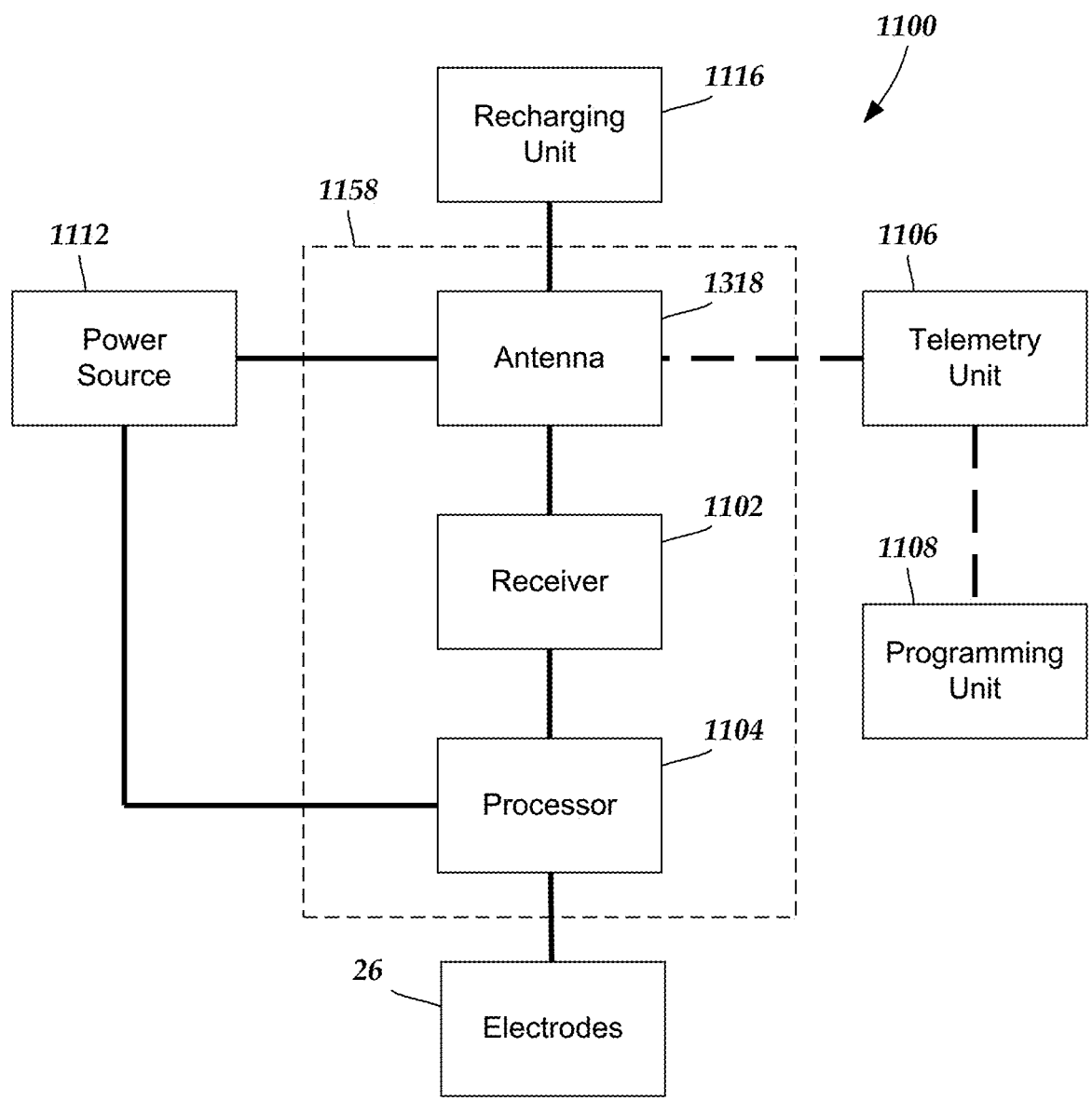
FIG. 11 is a schematic overview of one embodiment of components of a stimulation system, including an electronic subassembly disposed within a control module.

FIG. 11 is a schematic overview of one embodiment of components of an electrical stimulation system 1100 including an electronic subassembly 1158 disposed within a control module. The electronic subassembly 1158 may include one or more components of the IPG. It will be understood that the electrical stimulation system can include more, fewer, or different components and can have a variety of different configurations including those configurations disclosed in the stimulator references cited herein.

Some of the components (for example, a power source 1112, an antenna 1118, a receiver 1102, and a processor 1104) of the electrical stimulation system can be positioned on one or more circuit boards or similar carriers within a sealed housing of an implantable pulse generator (see e.g., 14 in FIG. 1), if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1118 or a secondary antenna. In at least some embodiments, the antenna 1118 (or the secondary antenna) is implemented using the auxiliary electrically-conductive conductor. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above. The electronic subassembly 1158 and, optionally, the power source 1112 can be disposed within a control module (e.g., the IPG 14 or the ETS 20 of FIG. 1).

In one embodiment, electrical stimulation signals are emitted by the electrodes 26 to stimulate nerve fibers, muscle fibers, or other body tissues near the electrical stimulation system. The processor 1104 is generally included to control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 selects which electrode(s) are cathodes and which electrode(s) are anodes. In some embodiments, the processor 1104 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by the programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and the receiver 1302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include the antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation system, comprising:
   at least one electrical stimulation lead, each of the at least one electrical stimulation lead comprising a plurality of stimulation electrodes; and
   a processor coupled to the at least one electrical stimulation lead and configured to perform actions, comprising:
      directing delivery of at least one therapeutic waveform through at least one of the stimulation electrodes of the at least one electrical stimulation lead to tissue of a patient during each of a plurality of therapeutic periods;
      directing sensing of an electrical signal using at least one of the stimulation electrodes of the at least one electrical stimulation lead during each of a plurality of sensing periods, wherein the therapeutic periods alternate with the sensing periods; and
      directing delivery of at least one sensing waveform from the electrical stimulation system through at least one of the stimulation electrodes of the at least one electrical stimulation lead during at least one of the sensing periods, wherein the at least one sensing waveform is a biphasic waveform comprising a positive phase and a negative phase.

2. The electrical stimulation system of claim 1, wherein directing sensing comprises, during at least one of the sensing periods, directing the sensing of the electrical signal without delivering a waveform through the stimulation electrodes.

3. The electrical stimulation system of claim 1, wherein parameters for the at least one sensing waveform differ from parameters for the at least one therapeutic waveform.

4. The electrical stimulation system of claim 1, wherein directing delivery of the at least one sensing waveform comprises, for a set of consecutive sensing periods, directing delivery of the at least one sensing waveform from one or more different electrodes during each one of the sensing periods of the set.

5. The electrical stimulation system of claim 1, wherein the at least one therapeutic waveform is a biphasic therapeutic waveform comprising a positive phase and a negative phase and directing delivery of the at least one therapeutic waveform and directing delivery of the at least one sensing waveform comprises, for a pair of consecutive therapeutic and sensing periods, directing delivery of a one of the at least one therapeutic waveform during the therapeutic period with a first temporal order of the positive and negative phases of the one of the at least one therapeutic waveform and directing delivery of a one of the at least one sensing waveform during the sensing period with a second temporal order of the positive and negative phases of the one of the at least one sensing waveform that is opposite the first temporal order.

6. The electrical stimulation system of claim 1, wherein an amplitude of the at least one sensing waveform is larger than an amplitude of the at least one therapeutic waveform and a pulse width of the at least one sensing waveform is shorter than a pulse width of the at least one therapeutic waveform.

7. The electrical stimulation system of claim 1, wherein the therapeutic periods are longer or shorter in time than the sensing periods.

8. The electrical stimulation system of claim 1, wherein the therapeutic periods comprise a plurality of first therapeutic periods and a plurality of second therapeutic periods, wherein the first and second therapeutic periods alternate, wherein the at least one therapeutic waveform comprises at least one first biphasic therapeutic waveform and at least one second biphasic therapeutic waveform,
   wherein directing the delivery of the at least one therapeutic waveform comprises:
      directing delivery of a one of the at least one first biphasic therapeutic waveform through at least one of the stimulation electrodes of the at least one electrical stimulation lead to tissue of a patient during the first therapeutic periods, wherein the one of the at least one first biphasic therapeutic waveform comprises a first phase and a second phase which occurs after the first phase and is opposite in polarity to the first phase; and
      directing delivery of a one of the at least one second biphasic therapeutic waveform through at least one of the stimulation electrodes of the at least one electrical stimulation lead to tissue of the patient during the second therapeutic periods, wherein the one of the at least one second biphasic therapeutic waveform comprises a third phase and a fourth phase which occurs after the third phase, wherein the third phase is opposite in polarity to both the first phase and the fourth phase.

9. The electrical stimulation system of claim 8, wherein the electrical signal comprises a first electrical signal and a second electrical signal,
   wherein directing sensing of the electrical signal comprises:
      after each the first therapeutic periods, directing sensing of the first electrical signal using at least one of the stimulation electrodes of the at least one electrical stimulation lead after delivery of the one of the at least one first biphasic therapeutic waveform;
      after each the second therapeutic periods, directing sensing of a second electrical signal using at least one of the stimulation electrodes of the at least one electrical stimulation lead after delivery of the one of the at least one second biphasic therapeutic waveform; and
      combining the first and second electrical signals to reduce at least one artifact arising in the sensing of the first and second electrical signals.

10. The electrical stimulation system of claim 9, the actions further comprise scaling at least one of the first or second electrical signals prior to combining the first and second electrical signals.

11. The electrical stimulation system of claim 9, wherein combining the first and second electrical signals comprises adding or averaging the first and second electrical signals.

12. The electrical stimulation system of claim 8, wherein the at least one first biphasic therapeutic waveform and the at least one second biphasic therapeutic waveform are asymmetric.

13. The electrical stimulation system of claim 8, wherein the at least one first biphasic therapeutic waveform and the at least one second biphasic therapeutic waveform are the same except for temporal phase ordering.

14. The electrical stimulation system of claim 8, wherein the therapeutic periods are longer or shorter in time than the sensing periods.

15. The electrical stimulation system of claim 1, wherein the at least one therapeutic waveform comprises at least one first therapeutic waveform and at least one second therapeutic waveform,
wherein directing the delivery of the at least one therapeutic waveform comprises:
a) directing delivery of a one of the at least one first therapeutic waveform through at least one of the stimulation electrodes of the at least one electrical stimulation lead to tissue of a patient; and
b) directing delivery of a one of the at least one second therapeutic waveform through at least one of the stimulation electrodes of the at least one electrical stimulation lead to tissue of the patient, wherein the one of the at least one first therapeutic waveform differs from the one of the at least one second therapeutic waveform in amplitude, pulse shape, pulse width, pulse period, electrode selection, or electrode fractionalization.

16. The electrical stimulation system of claim 15, wherein the electrical signal comprises a first electrical signal and a second electrical signal,
wherein directing sensing of the electrical signal comprises:
directing sensing of the first electrical signal from the tissue using at least one of the stimulation electrodes of the at least one electrical stimulation lead after delivery of the one of the at least one first therapeutic waveform;
directing sensing of the second electrical signal from the tissue using at least one of the stimulation electrodes of the at least one electrical stimulation lead after delivery of the one of the at least one second therapeutic waveform; and
using the first and second electrical signals to adjust at least one of the at least one first therapeutic waveform or the at least one second therapeutic waveform.

17. The electrical stimulation system of claim 16, wherein the at least one therapeutic waveform further comprises at least one third therapeutic waveform and the at least one electrical signal further comprises a third electrical signal, wherein the actions further comprise
after directing delivery of the one of the at least one first therapeutic waveform and the one of the at least one second therapeutic waveform, directing delivery of a one of the at least one third therapeutic waveform through at least one of the stimulation electrodes of the at least one electrical stimulation lead to tissue of the patient, wherein the one of the at least one third therapeutic waveform differs from the one of the at least one first therapeutic waveform and the one of the at least one second therapeutic waveform in amplitude or pulse width; and
directing sensing of the third electrical signal from the tissue using at least one of the stimulation electrodes of the at least one electrical stimulation lead after delivery of the one of the at least one third therapeutic waveform.

18. The electrical stimulation system of claim 15, wherein the at least one first therapeutic waveform and the at least one second therapeutic waveform are biphasic therapeutic waveforms with a positive phase and a negative phase.

19. The electrical stimulation system of claim 18, wherein the actions further comprise repeating steps a) and b) except reversing a temporal order of the positive phase and negative phase of the one of the at least one first therapeutic waveform and the one of the at least one second therapeutic waveform.

20. The electrical stimulation system of claim 15, wherein the therapeutic periods are longer or shorter in time than the sensing periods.

* * * * *